(12) United States Patent
Liu

(10) Patent No.: US 7,378,245 B2
(45) Date of Patent: *May 27, 2008

(54) METHODS FOR DETECTING AND LOCALIZING DNA MUTATIONS BY MICROARRAY

(75) Inventor: Guowen Liu, Eugene, OR (US)

(73) Assignee: State of Oregon Acting by and Through the State Board of Higher Education on Behalf of the University of Oregon, Eugene, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/605,826

(22) Filed: Nov. 28, 2006

(65) Prior Publication Data

US 2007/0184468 A1    Aug. 9, 2007

Related U.S. Application Data

(63) Continuation of application No. 10/236,598, filed on Sep. 6, 2002, now Pat. No. 7,141,371.

(51) Int. Cl.
 *C12Q 1/68* (2006.01)
 *C12P 19/34* (2006.01)

(52) U.S. Cl. ......................................... 435/6; 435/91.1

(58) Field of Classification Search .................... 435/6, 435/91.1
 See application file for complete search history.

(56) References Cited

U.S. PATENT DOCUMENTS

| | | | |
|---|---|---|---|
| 4,794,075 A | 12/1988 | Ford et al. | |
| 5,698,400 A | 12/1997 | Cotton et al. | |
| 5,723,320 A | 3/1998 | Dehlinger | |

(Continued)

FOREIGN PATENT DOCUMENTS

WO    WO 99/31272    6/1999

(Continued)

OTHER PUBLICATIONS

Buckley, "Development and Application of Microarray-Based Comparative Genomic Hybridization: Analysis of Neurofibromatosis Type-2, Schwannomatosis and Related Tumors," Abstract for Doctoral Thesis from Uppsala University, *Comprehensive Summaries of Uppsala Dissertations from the Faculty of Medicine* (Feb. 2005).

(Continued)

*Primary Examiner*—Kenneth R. Horlick
(74) *Attorney, Agent, or Firm*—Klarquist Sparkman LLP

(57) ABSTRACT

This disclosure provides methods for detecting and localizing DNA mutations by DNA microarray. In various embodiments, the described methods include use of restriction endonuclease(s) and/or mismatch-recognition nuclease(s) to detect and/or localize mutations. In one representative method, reference and target DNA are digested using one or more restriction endonucleases, resultant DNA strands are labeled (e.g., using a DNA polymerase), and the labeled mixture of DNAs is hybridized to a microarray. In another representative method, reference and target DNA are denatured and annealed to form a mixture containing heteroduplex DNA, one or more mismatch-recognition nuclease(s) are used to nick or cleave at least a portion of the heteroduplex DNA, resultant DNA strands are labeled (e.g., using a DNA polymerase) and the labeled mixture of DNAs is hybridized to a microarray.

14 Claims, 4 Drawing Sheets

U.S. PATENT DOCUMENTS

| | | | |
|---|---|---|---|
| 5,728,524 | A | 3/1998 | Sibson |
| 5,750,335 | A | 5/1998 | Gifford |
| 5,922,535 | A | 7/1999 | Huo |
| 6,468,742 | B2 | 10/2002 | Nerenberg |
| 6,713,258 | B2 | 3/2004 | Kilian |
| 6,783,943 | B2 | 8/2004 | Christian et al. |
| 6,924,104 | B2 | 8/2005 | Weissman et al. |
| 2002/0146723 | A1 | 10/2002 | Krontiris et al. |
| 2003/0186279 | A1 | 10/2003 | Kennedy |
| 2004/0048257 | A1 | 3/2004 | Liu |
| 2005/0032082 | A1 | 2/2005 | Kilian |
| 2005/0064406 | A1 | 3/2005 | Zabarovsky |

FOREIGN PATENT DOCUMENTS

| | | |
|---|---|---|
| WO | WO 00/34518 | 6/2000 |
| WO | WO 00/44936 | 8/2000 |
| WO | WO 00/50632 | 8/2000 |
| WO | WO 00/55364 | 9/2000 |
| WO | WO 02/083955 | 10/2002 |
| WO | WO 2004/044225 | 5/2004 |

OTHER PUBLICATIONS

Chee et al., "Accessing Genetic Information with High-Density DNA Arrays," *Science*, 274(5287):610-614 (Oct. 1996).

Gotoh and Oishi, "Screening of Gene-Associated Polymorphisms by Use of In-Gel Competitive Reassociation and EST (cDNA) Array Hybridization," *Genome Research*, 13:492-495 (2003).

Hacia, "Resequencing and mutational analysis using oligonucleotide microarrays," *Nature Genetics Supplement*, 21:42-47 (Jan. 1999).

Jaccoud et al., "Diversity Arrays: a solid state technology for sequence information independent genotyping," *Nucleic Acids Research*, 29 (4): 1-7 (2001).

Jingfeng et al., "NotI subtraction and NotI-specific microarrays to detect copy number and methylation changes in whole genomes," *PNAS USA* 99(16):10724-10729 (Aug. 6, 2002).

Liu et al., "SNP selection for a microarray based high-throughput genotyping assay," Abstract for a poster presented at Jul. 31-Aug. 4, 2004, meeting—12th International Conference on Intelligent Systems for Molecular Biology (accessible on-line at the website iscb.org/ismb2004/posters/guoying_liuATaffymetrix.com_463.html).

Lucito et al., "Representational Oligonucleotide Microarray Analysis: A High-Resolution Method to Detect Genome Copy Number Variation," *Genome Research*, 13:2291-2305 (2003).

Martin et al., "A rapid method to map mutations in *Drosophila*," *Genome Biology*, 2(9):1-12 (Aug. 2001).

Wang et al., "Large-Scale Identification, Mapping, and Genotyping of Single-Nucleotide Polymorphisms in the Human Genome," *Science*, 280:1077-1082 (May 1988).

Figure 3A
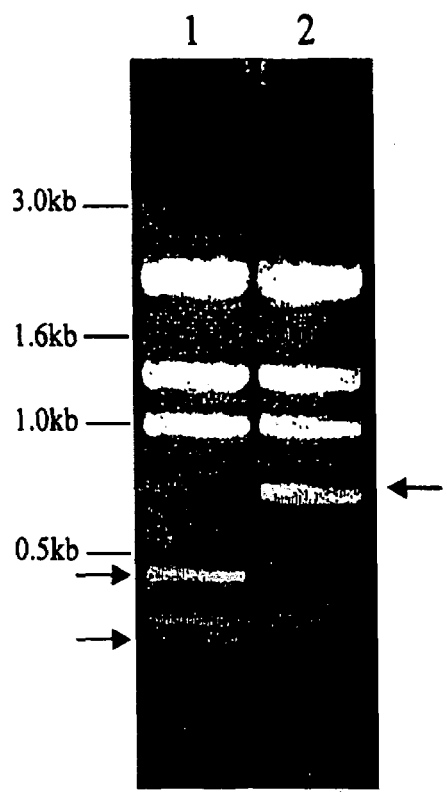
Figure 3B
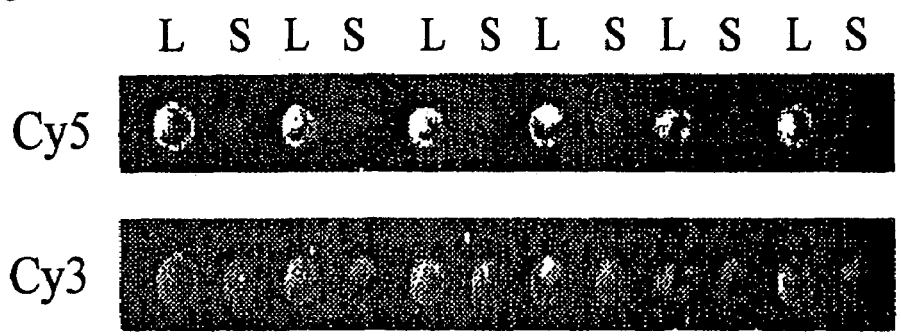
Figure 3

METHODS FOR DETECTING AND LOCALIZING DNA MUTATIONS BY MICROARRAY

CROSS-REFERENCE TO RELATED APPLICATION

This is a continuation of application Ser. No. 10/236,598, filed Sep. 6, 2002, now U.S. Pat. No. 7,141,371, issued Nov. 28, 2006, the entire disclosure of which is incorporated herein by reference.

BACKGROUND OF THE INVENTION

Detection and identification of simple nucleotide mutations and/or polymorphisms among individuals are very important in many biological fields, ranging from biomedical research in hereditary diseases to ecology and evolutionary biology. Identification of the location of mutations involved in heritable diseases can provide clues for the diagnosis, prognosis and therapeutic treatment of such diseases. However, it is very difficult to localize most of the mutations into a very small region (several kilo-base pairs) or a single gene at a genomic level.

Sequencing of the genome of different individuals is the most straightforward method for mutation detection, but it is expensive and time-consuming. Some methods have been developed to detect mutations without direct sequencing. Linkage and association mapping use polymorphic markers to approximate the chromosomal location of the mutations. This method is very efficient to localize a mutation into a quite large genomic region (several hundreds kilo-base pairs), but very slow to further localize it into a single gene or a small region (several kilo-base pairs). Restriction fragment length polymorphism (RFLP) is good for mutation detection and sequence comparison but can not efficiently define the location of a mutation either if whole genomic DNA is used as the starting material.

Most of the currently developed methods or techniques are suitable for testing mutations in a small region or a handful of genes, but are not good (if not impossible) for localizing mutations or polymorphisms at a genomic level. For example, in polynucleotide microarray hybridization methods (e.g. U.S. Pat. No. 5,837,832 (Chee et al.), and U.S. Pat. No. 6,376,191 (Yu et al.)) mutations in every single base position are detected by a set of four primers. To fully detect a 10 kb region, these methods will need about 10,000 sets of primers to be spotted on a microarray slide. Single stranded conformational polymorphism (SSCP) and denaturing gradient gel electrophoresis (DGGE) (Orita et al (1989) PNAS 86:2766; Myers et al (1985) N. A. R. 13:3131; White et al (1992) *Genomics* 5:301; Mills et al (1994) *Biochem.* 33:1797) methods are based on the observations that DNA sequence variations can cause DNA electrophoretic mobility changes. These two methods only work with short DNA molecules and can not screen many genes simultaneously.

The two methods I present in this invention have great potential to detect and localize DNA mutations at a genomic level simultaneously and rapidly. The method using restriction endonuclease(s) to detect mutations is termed RE microarray method. The other method using mismatch-recognition endonuclease(s) is named MR microarray method. The principle of the methods is illustrated in FIG. 1.

BRIEF SUMMARY OF THE INVENTION

Mutation detection is very important for the diagnosis, prognosis and therapeutic treatment of heritable diseases. However, none of the known methods can efficiently detect and define the location of mutations at a genomic level. In this invention, two methods are provided for such a purpose. The RE mutation detection microarray method used restriction endonuclease to detect mutations and the MR microarray method used mismatch-recognition nuclease to detect mutations. In the RE microarray method, the reference and target DNAs were completely digested with a restriction endonuclease. If a mutation caused the elimination of a restriction site of the endonuclease, the two restriction fragments in the reference DNA flanking the position of the mutation would in the target DNA become one large fragment spanning the position of the mutation. After denaturation and annealing, one single strand from the above two fragments of the reference DNA could anneal with one strand of the above large fragment of the target DNA to form a partially double-stranded DNA and DNA polymerase could then use the short strand of this DNA as a primer and the long strand as a template to label the short strand DNA by incorporating fluorescent nucleotides into newly synthesized DNA. Therefore, by this mechanism only the DNA strands flanking the mutation could be labeled. When hybridized to a microarray slide, the labeled DNA would bind to the spot whose DNA has the same sequence as the labeled DNA. By identification of the sequence of the spot DNA, the mutation would then be localized at or around this DNA sequence region, which can be as small as several kilo-bases. Similarly, a mutation that created a restriction site of the applied restriction endonuclease can also be detected and localized by this method.

In the MR mutation detection microarray method, reference DNA and target DNA were mixed, fragmented (by a restriction endonuclease), denatured and annealed to form heteroduplex DNA (between a single strand of a reference DNA fragment and a strand of the corresponding target DNA fragment carrying a mutation) as well as homoduplex DNA. The heteroduplex DNA was then specifically recognized and cleaved around the mismatch site into two short fragments by a mismatch-recognition nuclease while its corresponding homoduplex DNA and other homoduplex DNA would not be cleaved and kept full length. After re-denaturation and re-annealing of the nuclease-treated DNA mixture, a single strand of the cleaved short DNA fragments could anneal to a single strand of its corresponding full length DNA fragment to form a partially double-stranded DNA. As described in the RE microarray method, DNA polymerase could then use this partially double-stranded DNA to label the DNA strands flanking the mutation and after hybridization to a DNA microarray the location of the mutation would be identified.

In practice, both methods also used a differently labeled control DNA. The control DNA is the reference DNA alone or the target DNA alone treated in the same way as the mixture of the reference and target DNA as described above but labeled differently from the mixture of reference and target DNA. The differently labeled control DNA would then be combined with the labeled mixture DNA and hybridized to a microarray slide. The mutations would be detected and localized by identifying the sequence of each DNA whose microarray spot had a higher ratio of the label signal from the mixture DNA to the label signal from the control DNA. Such a control could reduce the effect of non-specific cutting or digestion by the nuclease and varied DNA amounts of different microarray spots, etc.

To prove the practicability of the methods, mutations in plasmids were detected and localized. A wild type plasmid was divided into two regions, L and R, and two DNA molecules separately from the two regions were used to spot onto slides to make mini microaffays. Three mutant plasmids (target DNAs) were compared with the wild type parental plasmid (reference DNA) by the methods. One of the mutant plasmids had a mutation that caused the elimination of an Ase I restriction site and the RE mutation detection microarray method successfully detected and localized the mutation into the L region. The other two mutant plasmids each had a single nucleotide mutation and the MR mutation detection microaffay method correctly detected and identified the location of the mutations. These experimental results indicate that the methods are practical and successful in mutation detection.

BRIEF DESCRIPTION OF THE DRAWINGS

FIG. 3a shows the difference of restriction patterns between a wild type plasmid and a mutant plasmid where an Ase I site is missing.

FIG. 3b shows that the mutation that caused the missing of an Ase I site in a mutant plasmid can be detected and correctly localized by the RE microarray method.

DETAILED DESCRIPTION OF THE INVENTION

Materials used in this invention are listed as follows:

All the restriction endonucleases used were from New England Biolabs Inc. Taq DNA polymerase, its reaction buffer and dNTPs were from Roche Applied Science. QIAquick gel extraction kit was used for isolating DNA fragments from agarose gel and QIAquick PCR purification kit was used to purify DNA fragments from enzymes, nucleotides and salts (from Qiagen GmbH). Cy3 and Cy5-labeled dCTPs were from Amersham Biosciences.

Wild type (reference DNA) and mutant plasmids (target DNAs) used in this work were from Tom H. Stevens lab at the University of Oregon. pKH28 was constructed by inserting a 795bp fragment carrying a wild type VMA21 gene in between the Sac I and Kpn I sites of pRS 316. pLG119 has a T to A substitution at 2106bp. pLG120 has an A to C substitution at 2109bp and pLG 125 has an adjacent two nucleotides substitution (AT to GC) at 2126bp and 2127bp, which happens to eliminate an Ase I cutting site (ATTAAT) by changing the first AT to GC. In this work pKH28 is called wild type plasmid DNA or reference DNA. pLG119, 120 and 125 are called mutant plasmid DNA or target DNA.

Figure 1:
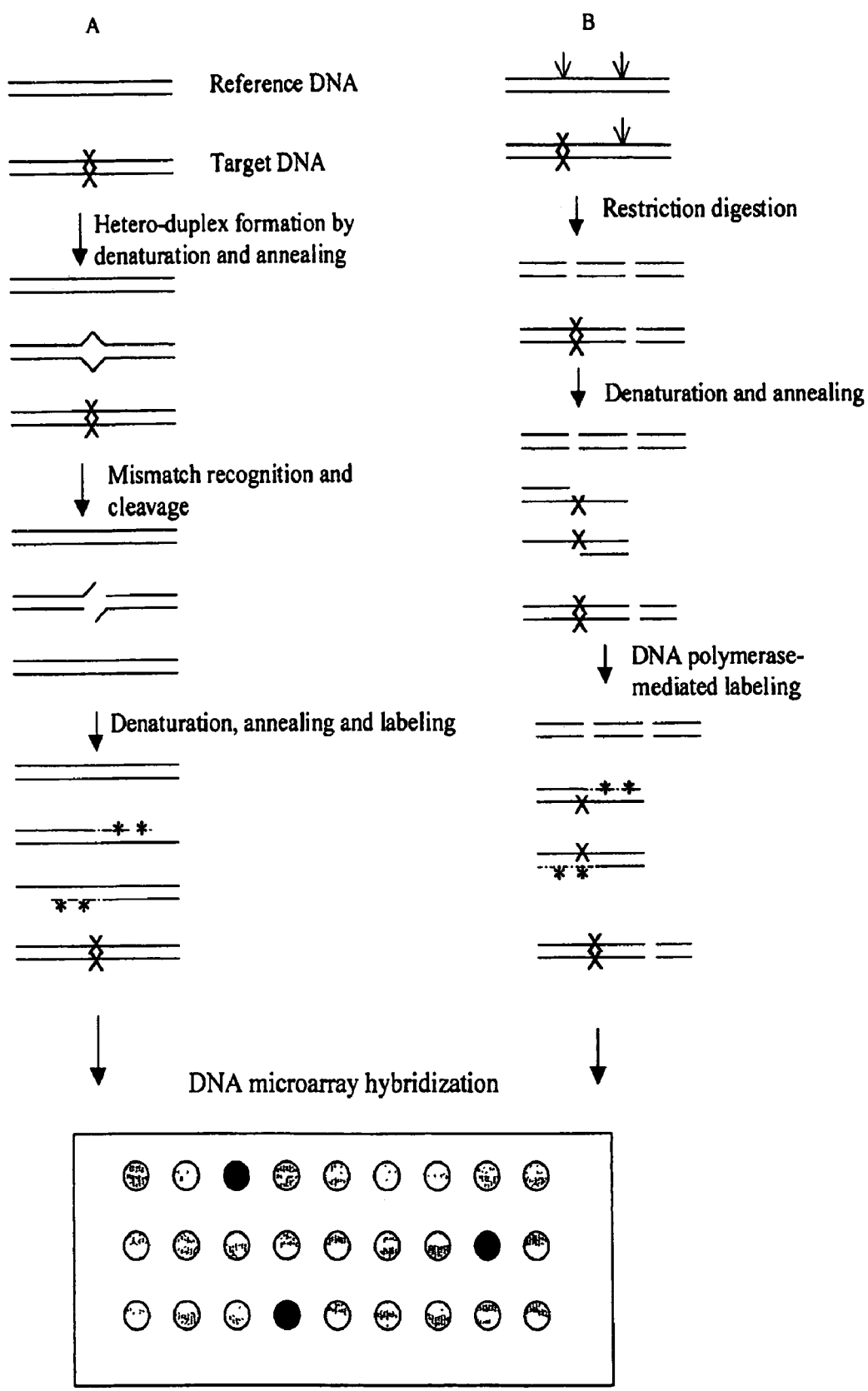
FIG. 1 depicts the principal of the method.
Figure 2:
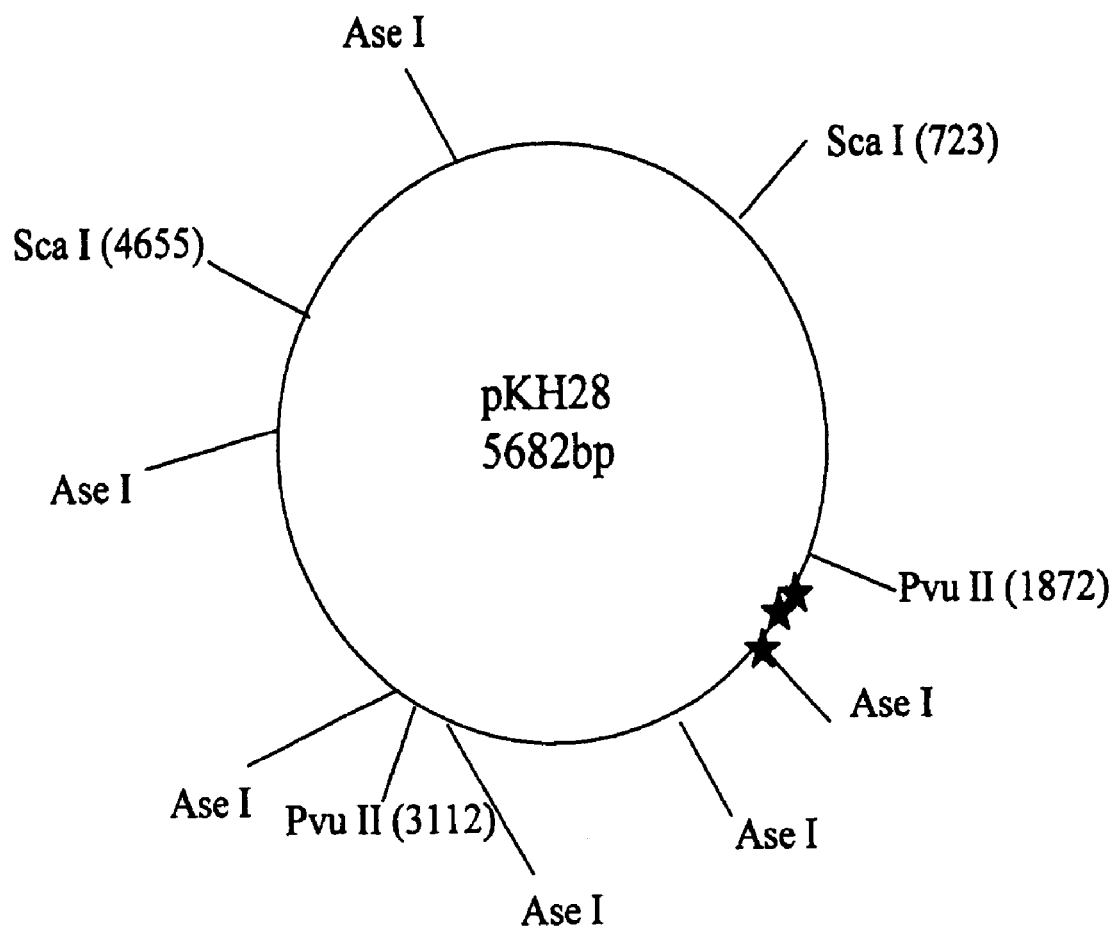
FIG. 2 shows the map of the parental plasmid DNA. The locations of the mutations in target plasmid are also indicated.

The DNA microarray slides were made according to the protocols published at web site http://www.microarrays.org, which is maintained by Stanford University. Plasmid pKH28 and its derivatives pLG119, 120 and 125 all have two Sca I restriction sites (FIG. 2). In this invention, the two Sca I sites were used to separate the plasmid into two regions (L and S) (see FIG. 2) and the novel methods were tested to see if it could localize the mutations into a correct region. Therefore, a very simple DNA microarray was made, which only contains two different DNA molecules: a large Sca I fragment molecule (L region DNA) and a small Sca I fragment molecule (S region DNA). These two DNA fragments were isolated from plasmid pKH28 DNA after digestion with Sca I, separation on agarose gel and purification. The two DNAs were spotted onto glass slides in a tandem repeat order as L, S for six times. Therefore, there are six spots for each DNA per microarray slide.

Cel I nuclease, a mismatch-recognition enzyme, was prepared from celery according to a published method (Yang et al (2000) *Biochem*. 39:3533) with some modifications and less steps of purification. Briefly, 10 kg of fresh celery stalks was homogenized with a juicer and the juice was collected and adjusted to the composition of buffer A (100 mM Tris-HCl, pH7.7, 0.5 M KCL and 100 µM PMSF). The suspension was centrifuged at 8000 g for 30 min and the supernatant was collected. 10 ml of Concanavalin A-sepharose (from Sigma) resin was added into the cleared supernatant and gently shaken overnight at 4° C. The resin was then pelleted and washed twice with buffer A by two cycles of centrifugation (at 3000 g for 30 min) and resuspended. Cel I was then eluted from the resin with 80 ml of buffer A containing 0.3 M α-methyl-mannoside by incubation at 4° C. for four hours with gentle shaking. After centrifugation, the Cel I nuclease solution (supernatant) was collected, aliquot and stored at −20° C. When needed, an aliquot of the enzyme would be thawed and used. For the cleavage of mismatched double-stranded DNA, the best condition for a reaction of 2 µg DNA in a 30 µl final volume in 1X Cel I reaction buffer (20 mM Tris-HCl pH7.4, 25 mM KCL, 10 mM $MgCl_2$ was 1 µl of this Cel I preparation and 30 min incubation at 37° C.

The following examples are intended to illustrate the present invention and should in no way be construed as limiting the invention.

EXAMPLE 1

Detection and Localization of DNA Mutations by the RE Mutation Detection Microarray Method Restriction fragment length polymorphism (RFLP) is one of the most popularly used methods for mutation detection and sequence comparison. However, it can not define the location of the mutation. In this experiment, a microarray method is developed for rapid detection and localization of DNA mutations.

A mutation in a mutant plasmid pLG125 caused the missing of an Ase I site, which is present in the wild type plasmid pKH28 (see Materials and FIG. 2).

One microgram (µg) each of pLG125 and pKH28 was double digested with Pvu II and Ase I in NEB buffer 2 plus BSA, purified with QlAquick PCR purification kit and resuspended in 30 microliters (µl) of EB buffer (10 mM Tris-HCl, pH8.0). 5 µl of the above digested pKH28 DNA was mixed with 5 µl of the above pLG125 DNA to give a hetero-mixture DNA. 10 µl of the above digested pKH28 was also taken and called a control DNA. To label the DNA, the following chemicals were added to each of the mixtures: 2 µl of Taq DNA polymerase buffer (with 2.0 mM $MgSO_4$,5 µl of dATP, dTTP and dGTP mixture each at a concentration of 2 mM, 1 µl of 2 mM dCTP, 1 µl of 1mM Cy5-dCTP (for hetero-mixture DNA) or Cy3-dCTP (for the control DNA), and 1 µof Taq DNA polymerase (1 unit). A PCR machine was then used to complete the labeling reaction by a program that the first step is 95° C. 2 min to denature double-stranded DNA, then run 15 cycles of 95° C. 1 min and 72° C. 2 min, followed by a step of 72° C. 15 min and finally stop the reaction by quickly cooling to 4° C. The labeled reaction mixtures were combined, purified by QIAquick PCR purification kit and eluted with 30 µl of EB buffer (10 mM Tris-HCl, pH8.0). 10.5 µl was taken out to mix with 3 µl of 20X SSC, 1.1 µl 20 mg/ml polyA and 0.42 µl of 10% SDS. After being heated at 100° C. for 2 min and briefly centrifuged, the mixture was then loaded onto a microarray slide for hybridization at 65° C. for 4-16 hours. After scanning of the microarray slides, it was found that in the same microarray slide the Cy5/Cy3 ratio of any spot of the L region DNA was about 5 to 9 times higher than that of any spot of the S region DNA (see FIG. 3). This clearly localizes the mutation in the L region in pLG125 plasmid, which is correct, indicating this method is feasible in mutation detection and localization.

EXAMPLE 2

Detection and Localization of DNA Mutations by the MR Mutation Detection Microarray Method This experiment comprises four major steps: formation of heteroduplex and homoduplex DNA; treatment of the duplexes with a mismatch-recognition endonuclease to cleave the heteroduplexes at the mismatch site; labeling the cleaved DNA by DNA polymerase-mediated incorporation of modified nucleotides; and hybridizing the labeled DNA to DNA microarray.

There are a few mismatch-recognition endonucleases such as SP nuclease and Mung Ben nuclease. Here, Cel I nuclease was chosen because of its high specificity of cleavage at all single nucleotide substitutions (Oleykowski et al (1998) *Nucleic Acids Research* 26: 4597).

To detect and localize a mutation in plasmid pLG119, both pLG119 and wild-type plasmid pKH28 were digested with Sca I and then purified with QIAquick PCR purification kit. One microgram of this Sca I-digested pLG119 (pLG119/Sca I) was mixed with one microgram of the Sca I-digested pKH28 (pKH28/Sca I) in 30 microliters of 2X Cel I reaction buffer. As a control, two micrograms of the pKH28/Sca I were also resuspended in 30 µl of 2X Cel I reaction buffer and would experience exactly the same treatment as the wild type and mutant DNA mixture. The mixtures were then denatured at 95° C. for 5 min, cooled to 85° C. quickly and then slowly cooled down to 30° C. at a speed of 3° C. per hour. This denaturation and annealing step was processed in a PCR machine. In the pKH28/Sca I and pLG119/Sca I mixture, both homoduplexes and heteroduplexes would form randomly. The pKH28/Sca I control would be mainly homoduplexes.

Figure 4:
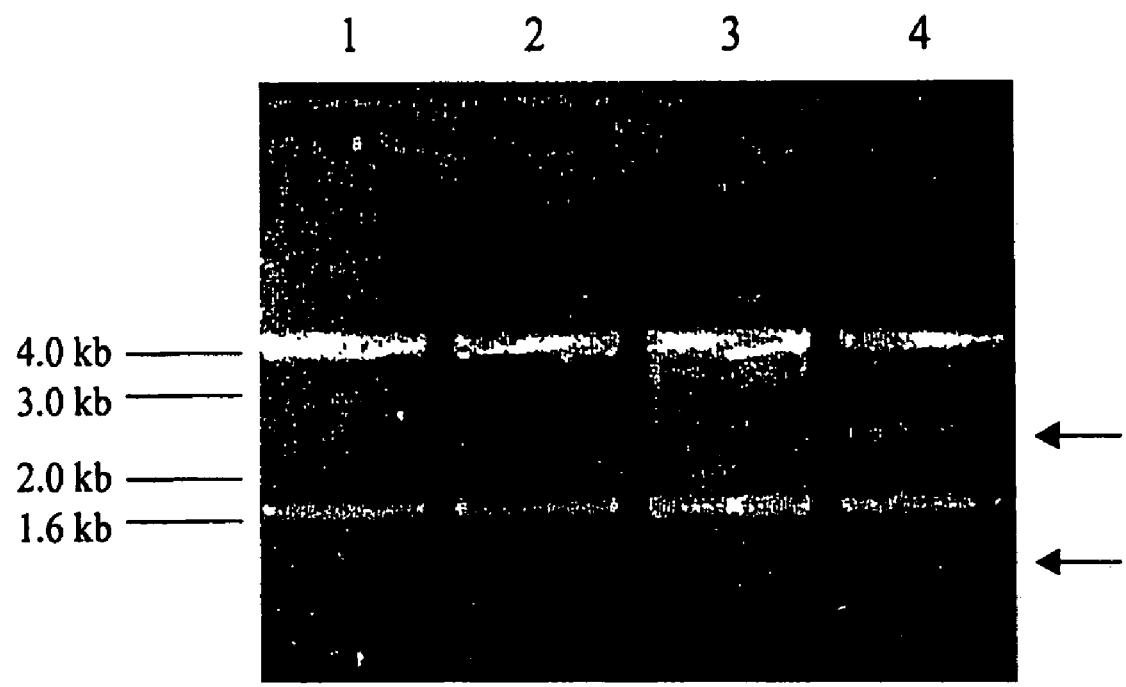
FIG. 4 shows the cleavage of a heteroduplex DNA by Cel I nuclease.

After the formation of heteroduplexes, 28 µl of sterile distilled water was added to each of the above DNA mixtures to get a total of 58 µl. To cleave heteroduplex DNA, 1 µl of Cel I preparation was added into 29 µl of each of the mixtures and incubated at 37° C. for 30 min. After immediate purification with a QIAquick PCR purification kit, each of the Cel I-treated DNA mixtures was resuspended in 30 µl of LB buffer (10 mM Tris-HCl, pH8.0). 6 µl of each was taken and loaded onto 1.0% agarose for gel electrophoresis. It was shown that Cel I could cleave heteroduplexes and produce two new smaller fragments (FIG. 4). It was also shown that Cel I had quite strong non-specific cutting because there was some smear on both of the lanes loaded with Cel I-treated DNA. This is consistent with a former publication (Sokurenko et al (2001) *Nucleic Acids Research* 29: e111), where Cel I caused significant non-specific digestion of duplex DNA.

To detect the cleaved DNA, Taq DNA polymerase was used to add fluorescent Cy3 or Cy5-dCTP onto it. For this purpose, 10 µl of each of the above purified Cel I-treated DNA was mixed with 2 µl of Taq DNA polymerase buffer (with 2.0 mM MgSO$_4$,5 µl of dATP, dTTP and dGTP mixtures each at a concentration of 2 mM, 1 µl of 2 mM dCTP, 1 µl of 1 mM Cy5-dCTP (for DNA from the mixture of pKH28/Sca I and pLG119/Sca I) or Cy3-dCTP (for the control DNA), and 1 µl of Taq DNA polymerase (1 unit). A PCR machine was then used to complete the labeling reaction by a program that the first step is 95° C. 2 min to denature double-stranded DNA, then run 15 cycles of 95° C. 1 min and 72° C. 2 min, followed by a step of 72° C. 15 min and finally stop the reaction by quickly cooling to 4° C. The labeled reaction mixtures were combined, purified by QIAquick PCR purification kit and eluted with 30 µl of LB buffer (10 mM Tris-HCl, pH8.0). 10.5 µl was taken out to mix with 3 µl of 20X SSC, 1.1 µl 20 mg/ml polyA and 0.42 µl of 10% SDS. After being heated at 100° C. for 2 min and briefly centrifuged, the mixture was then loaded onto a microaffay slide for hybridization at 65° C. for 4-16 hours.

The localization of the mutation can be achieved by comparing the ratios (Cy5/Cy3) of different DNA spots. With more than six repeats of the above experiments and each experiment with 6 repeated spots for each DNA fragment, it was found that in the same microarray slide the Cy5/Cy3 ratio of any spot of the L region DNA was 0.4-0.7 times higher than that of any spot of the S region DNA. This predicts that the mutation caffied by plasmid pLG119 was located on the large Sca I fragment, which is correct according to the known fact that the mutation is there. This indicates that though there is quite strong non-specific cutting by Cel I nuclease, this method was still able to detect and localize the DNA mutation.

Plasmid pLG120, which has an A to C substitution, was also used to test this method. A positive result very similar to that from pLG119 was obtained again. This further proved the practicability of this method and indicated the result of this method is repeatable and reliable. This method should work on genomic microarray in a similar way and then DNA mutations or polymorphisms in individual genomes would be able to be detected and localized rapidly.

I claim:

1. A method comprising:
   a) digesting reference and target DNA using a restriction endonuclease, wherein the restriction endonuclease digests the reference and the target DNA into different DNA fragments around one or more mutations that eliminates or creates a restriction site of the endonuclease, and mixing the reference and target DNA, thereby producing a digested mixture of reference and target DNA;
   b) labeling DNA strands of the digested mixture of reference and target DNA flanking the one or more mutations by one or more cycles of denaturation, annealing and labeling with a DNA polymerase, wherein denaturation and annealing allows annealing of the different DNA fragments around one or more mutations from reference and target DNA to form a partially double-stranded DNA duplex, and wherein the DNA polymerase labels the DNA of the partially double-stranded duplex by incorporating modified nucleotides into newly synthesized DNA, thereby producing a labeled mixture of reference and target DNA;
   c) hybridizing a combination of the labeled mixture of reference and target DNA and a labeled control DNA to at least one DNA array, which array comprises spots comprising at least one DNA probe, at least one of the spots comprising a DNA probe from the target DNA or the reference DNA or both, and wherein the labeled control DNA is (i) reference DNA alone or (ii) target DNA alone, treated substantially as in a) and b) but labeled with a distinguishable modified nucleotide; and (d) identifying the sequence of DNA of at least one spot of the DNA array that has significantly higher ratio of label signal from the mixture of reference and target DNA compared to label signal from the control DNA, thereby detecting and localizing one or more mutations in the target DNA as compared to the reference DNA.

2. The method of claim 1, wherein the restriction endonuclease is at least one restriction endonuclease or an agent that binds to specific DNA sequence and cleaves or nicks DNA at or near the specific sequence, or a combination of two or more thereof.

3. The method of claim 1, wherein the DNA polymerase is a DNA polymerase or a mixture of two or more different DNA polymerases.

4. The method of claim 1, wherein spots of the DNA array comprise DNA fragments covering a whole genome.

5. A method comprising:
a) forming a mixture of heteroduplex and homoduplex DNA by denaturing and annealing a mixture of reference and target DNA to form heteroduplex DNA, homoduplex reference DNA, and homoduplex target DNA;
b) treating the mixture of heteroduplex and homoduplex DNA with a mismatch-recognition molecule, thereby nicking or cleaving the heteroduplex DNA at or around a mismatch site;
c) labeling DNA strands by one or more cycles of denaturation, annealing and labeling with a DNA polymerase, wherein denaturation and annealing allows one short strand from the nicked or cleaved heteroduplex DNA to anneal with one long strand from homoduplex DNA spanning the same mismatch site to form a partially double-stranded DNA duplex, and wherein the DNA polymerase uses the short strand as a primer and the long strand as a template to label the short strand by incorporating modified nucleotides into newly synthesized DNA, thereby producing a labeled mixture of reference and target DNA;
d) hybridizing a combination of the labeled mixture of reference and target DNA and a labeled control DNA to at least one DNA array, which array comprises spots comprising at least one DNA probe, at least one of the spots comprising a DNA probe from the target DNA or the reference DNA or both, and wherein the labeled control DNA is (i) reference DNA alone or (ii) target DNA alone, treated substantially as in a) and b) but labeled with a distinguishable modified nucleotide; and
e) identifying the sequence of DNA of at least one spot of the DNA array that has a significantly higher ratio of label signal from the mixture of reference and target DNA compared to label signal from the control DNA, thereby detecting and localizing one or more mutations in the target DNA as compared to the reference DNA.

6. The method of claim 5, wherein the mismatch-recognition nuclease is at least one nuclease that cleaves or nicks heteroduplex DNA, or a mixture of different nucleases.

7. The method of claim 5, wherein the mismatch-recognition nuclease is a naturally existing nuclease, an artificial enzyme constructed by fusing a mismatch-recognition protein or peptide to a nuclease, or a combination thereof.

8. The method of claim 5, wherein the DNA polymerase is a DNA polymerase or a mixture of two or more different DNA polymerases.

9. The method of claim 5, wherein spots of the DNA array comprise DNA fragments covering a whole genome.

10. The method of claim 1, wherein the modified nucleotides are labeled nucleotides that comprise a label that is fluorescent, enzymatic, chemiluminescent or radioactive, or nucleotides conjugated to a molecule that binds to a label which is fluorescent, enzymatic, chemiluminescent or radioactive.

11. The method of claim 5, wherein the modified nucleotides are labeled nucleotides that comprise a label that is fluorescent, enzymatic, chemiluminescent or radioactive, or nucleotides conjugated to a molecule that binds to a label which is fluorescent, enzymatic, chemiluminescent or radioactive.

12. The method of claim 1, wherein c) further comprises reacting the newly synthesized DNA with an agent that labels the modified nucleotides.

13. The method of claim 5, wherein d) further comprises reacting the newly synthesized DNA with an agent that labels the modified nucleotides.

14. The method of claim 5, wherein the mixture of reference and target DNA is a mixture of fragmented reference and target DNA obtained by using at least one restriction endonuclease to digest the reference and target DNA.

* * * * *